(12) United States Patent
Salcedo et al.

(10) Patent No.: US 10,016,242 B2
(45) Date of Patent: Jul. 10, 2018

(54) SPLINT DEVICE FOR FORMING A FIDUCIAL MARKER FOR A SURGICAL ROBOT GUIDANCE SYSTEM, AND ASSOCIATED METHOD

(71) Applicant: NEOCIS INC., Miami, FL (US)

(72) Inventors: Juan Ricardo Salcedo, Coral Gables, FL (US); Alon Mozes, Miami Beach, FL (US); Manan Kishore Shah, Miami, FL (US); Ryan Anderson, Aventura, FL (US); Jeffrey Ganeles, Boca Raton, FL (US); Federico Grande, Stuart, FL (US); John Philip Kennedy, Duntroon (CA)

(73) Assignee: Neocis Inc., Miami, FL (US)

( * ) Notice: Subject to any disclaimer, the term of this patent is extended or adjusted under 35 U.S.C. 154(b) by 0 days.

(21) Appl. No.: 15/174,521

(22) Filed: Jun. 6, 2016

(65) Prior Publication Data

US 2017/0348055 A1     Dec. 7, 2017

(51) Int. Cl.
*A61B 34/10* (2016.01)
*A61C 1/08* (2006.01)
(Continued)

(52) U.S. Cl.
CPC .............. *A61B 34/10* (2016.02); *A61C 1/082* (2013.01); *A61C 5/007* (2013.01); *A61B 2034/2068* (2016.02); *A61B 2090/3983* (2016.02)

(58) Field of Classification Search
CPC ........... A61C 1/08; A61C 1/082; A61C 1/084; A61C 5/007; A61C 5/30; A61C 5/80;
(Continued)

(56) References Cited

U.S. PATENT DOCUMENTS 3,772,790 A * 11/1973 Swan-Gett ............... A61B 1/24
433/136
4,368,040 A * 1/1983 Weissman ............ A61C 9/0006
433/223
(Continued)

FOREIGN PATENT DOCUMENTS

| DE | 619 140 | 9/1935 |
| DE | 656 558 | 2/1938 |
| WO | WO 2015/104683 | 7/2015 |

*Primary Examiner* — Nicholas Lucchesi
*Assistant Examiner* — Shannel Wright
(74) *Attorney, Agent, or Firm* — Womble Bond Dickinson (US) LLP (57) ABSTRACT

A method of implementing a splint device, and associated splint device, are provided for a guidance system of a surgical robot. A splint body includes first and second stabilizing portions extending from opposed lateral sides of a medial portion, and defines a U channel. The medial portion, or the medial portion and one of the stabilizing portions, defines a bridge portion extending along the U channel. A partition member, received by the bridge portion, extends into and longitudinally along the U channel. An adhesive material is engaged with the splint body, within the U channel. The U channel is engaged about a tooth or jaw of a patient, and urged toward the tooth or jaw, such that the partition member engages the tooth or jaw and separates the adhesive material into a first portion engaged with the first stabilizing portion and a second portion engaged with the second stabilizing portion.

10 Claims, 7 Drawing Sheets

(51) Int. Cl.
*A61C 5/00* (2017.01)
*A61B 90/00* (2016.01)
*A61B 34/20* (2016.01)

(58) Field of Classification Search
CPC .... A61C 5/82; A61C 5/84; A61C 5/85; A61C 5/88; A61C 8/0089; A61C 9/0006; A61B 6/14; A61B 6/145; A61B 34/10; A61B 34/20; A61B 2034/2068; A61B 2090/3983
USPC .............................................. 433/75, 50, 72
See application file for complete search history.

(56) References Cited

U.S. PATENT DOCUMENTS

| | | | | |
|---|---|---|---|---|
| 4,459,107 A * | 7/1984 | Weissman | ............ | A61C 9/0006 433/213 |
| 4,557,692 A * | 12/1985 | Chorbajian | ............ | A61C 5/007 433/215 |
| 5,015,183 A * | 5/1991 | Fenick | ............ | A61C 1/084 433/173 |
| 5,026,278 A * | 6/1991 | Oxman | ............ | A61C 9/0006 433/37 |
| 5,173,048 A * | 12/1992 | Summer | ............ | A61C 19/05 433/215 |
| 5,516,286 A * | 5/1996 | Kushner | ............ | A61C 17/0211 433/136 |
| 9,402,691 B2 * | 8/2016 | Merritt | ............ | A61B 90/39 |
| 2002/0189620 A1 * | 12/2002 | L'Estrange | ............ | A61F 5/566 128/848 |
| 2005/0163342 A1 * | 7/2005 | Persky | ............ | A61B 6/14 382/103 |
| 2006/0257817 A1 * | 11/2006 | Shelton | ............ | A61C 8/0089 433/75 |
| 2008/0138755 A1 * | 6/2008 | Jansheski | ............ | A61F 5/566 433/6 |
| 2008/0171305 A1 * | 7/2008 | Sonenfeld | ............ | A61C 1/084 433/215 |
| 2008/0176187 A1 * | 7/2008 | Stumpel | ............ | A61C 1/084 433/196 |
| 2009/0253095 A1 * | 10/2009 | Salcedo | ............ | A61B 1/24 433/75 |
| 2011/0217667 A1 * | 9/2011 | Groscurth | ............ | A61C 9/004 433/68 |
| 2012/0148978 A1 * | 6/2012 | Suchan | ............ | A61C 9/0006 433/38 |
| 2013/0071810 A1 * | 3/2013 | Freitas | ............ | A61C 1/084 433/72 |
| 2014/0205968 A1 * | 7/2014 | Jung | ............ | A61C 3/02 433/75 |
| 2014/0272773 A1 * | 9/2014 | Merritt | ............ | A61B 5/0088 433/29 |
| 2014/0320600 A1 * | 10/2014 | Daon | ............ | H04N 13/02 348/45 |
| 2015/0010881 A1 * | 1/2015 | Llop | ............ | A61C 8/0089 433/75 |
| 2016/0038255 A1 * | 2/2016 | Llop | ............ | A61C 8/0089 433/75 |
| 2016/0074129 A1 * | 3/2016 | Merritt | ............ | A61B 90/39 433/29 |
| 2016/0184050 A1 * | 6/2016 | Chodorow | ............ | A61B 5/0013 433/27 |

* cited by examiner

SPLINT DEVICE FOR FORMING A FIDUCIAL MARKER FOR A SURGICAL ROBOT GUIDANCE SYSTEM, AND ASSOCIATED METHOD

BACKGROUND

Field of the Disclosure

The present application relates to surgical robots and associated guidance systems and, more particularly, to a splint device for forming a fiducial marker and/or a tracking marker for the guidance system of a surgical robot used, for example, in a surgical procedure associated with the head of a patient, such as dental surgery.

Description of Related Art

Robotic systems are being increasingly implemented in surgical applications. One such example involves a surgical robot used in dental surgery. Such robots are often associated with a guidance system used to guide the surgical instrument implemented by the surgical robot. The guidance system may also be configured to be involved in the surgical pre-planning process, whether by being involved in gathering and/or analyzing patient data, and planning the surgical procedure, or by relying upon pre-planning data to guide the surgical instrument to conduct the surgical procedure.

In particular surgical procedures, some surgical robotic systems rely upon a fixed reference point associated with the patient's body for guiding the surgical robot. That is, some such surgical robotic systems define a frame of reference with respect to the patient's body so as to account or otherwise compensate for movements or motion of the patient during the procedure, whether during pre-planning or during the actual surgical procedure itself. This reference point must also be repeatable such that multiple engagements/disengagements (i.e., periods between pre-planning and the actual surgical procedure) do not change the frame of reference implemented by the surgical robot or the guidance system associated therewith.

In particular instances, the reference point (or the connection between the guidance system and the patient to define that reference point) implemented by the guidance system for the surgical robot may be accomplished through, for example, an optical modality, a mechanical modality, an acoustic modality, or other suitable and appropriate tracking/guiding modality, or combination thereof. In some modalities, particularly used in dental surgery applications, one mechanical modality for forming the reference point (i.e., a "fiducial marker") may be accomplished, for example, by attaching/securing a rigid element to the head/teeth/jaw of the patient. Such a rigid element, in some instances, may be referred to as and may comprise a splint (see, e.g., prior art in FIGS. 1, 2A, and 2B). Such a splint may generally include, for instance, a retainer portion that grips the jaw or one or more of the teeth (i.e., by way of an adhesive substance, such as an acrylic material applied between the retainer portion and the teeth or jaw), a mounting portion (i.e., mounting arm 25) that connects the retainer portion to a kinematic mount, and the kinematic mount, itself, which may comprise an attachment point for a tracking portion associated with the guidance system for the surgical robot (i.e., wherein, for instance, reflective markers may be mounted to the attachment point for optical tracking of the fiducial marker, or the attachment point may include a securing site for forming a mechanical connection therewith for mechanical tracking of the fiducial marker, or the attachment point may otherwise be configured to receive an appropriate element associated with any other suitable tracking arrangement for the fiducial marker).

In such instances, it may be preferable for the retainer to be as rigid as possible (i.e., the structure of the retainer itself, as well as the fixation thereof to the teeth/jaw of the patient) throughout the surgical procedure. However, it may also be preferable for the retainer to be readily removable when the surgical procedure is complete. In some instances, it may be preferable for the retainer to be reproducibly removed and replaced, for example, between the pre-planning procedure (i.e., a CT scan) which may occur on one day (when the retainer must be in place so the fiducial marker(s) associated therewith are captured in the scan), and the surgical procedure may occur on another day (wherein the surgical procedure requires the retainer to be in place for tracking/guiding the surgical procedure).

Figure 1:
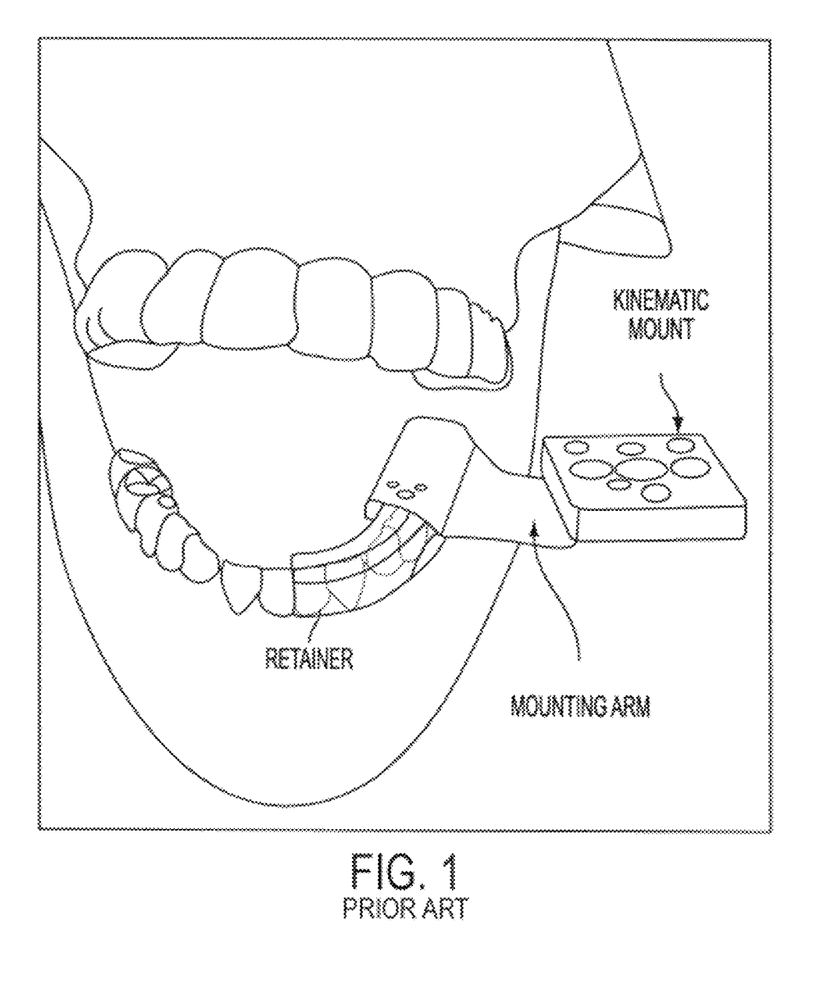
FIG. 1 schematically illustrates a prior art splint device engaged with a representative model of a mouth of a patient so as to provide a fiducial marker and/or a tracking marker for a guidance system for a surgical robot.
Figure 2A:
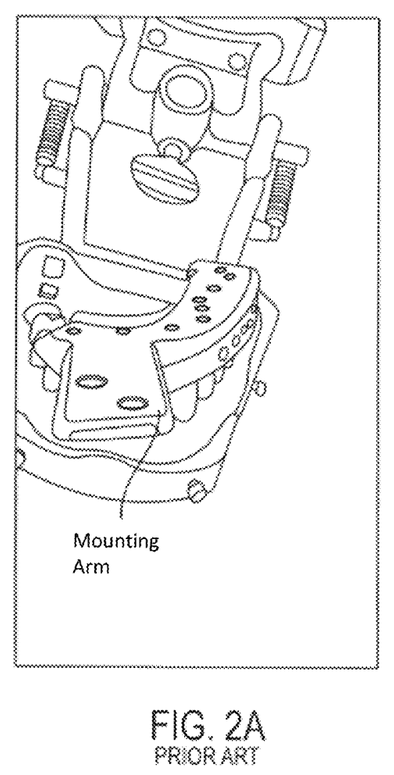
FIGS. 2A and 2B schematically illustrate a prior art splint device engaged with a representative model of a mouth of a patient so as to provide a fiducial marker and/or a tracking marker for a guidance system for a surgical robot (FIG. 2A) and the prior art splint device disengaged from the representative model of the mouth of the patient (FIG. 2B)
Figure 2B:
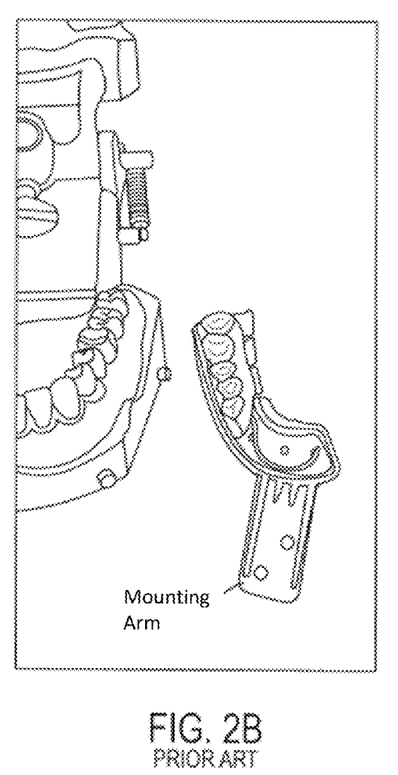
Figures 3A, 3B, 3C:
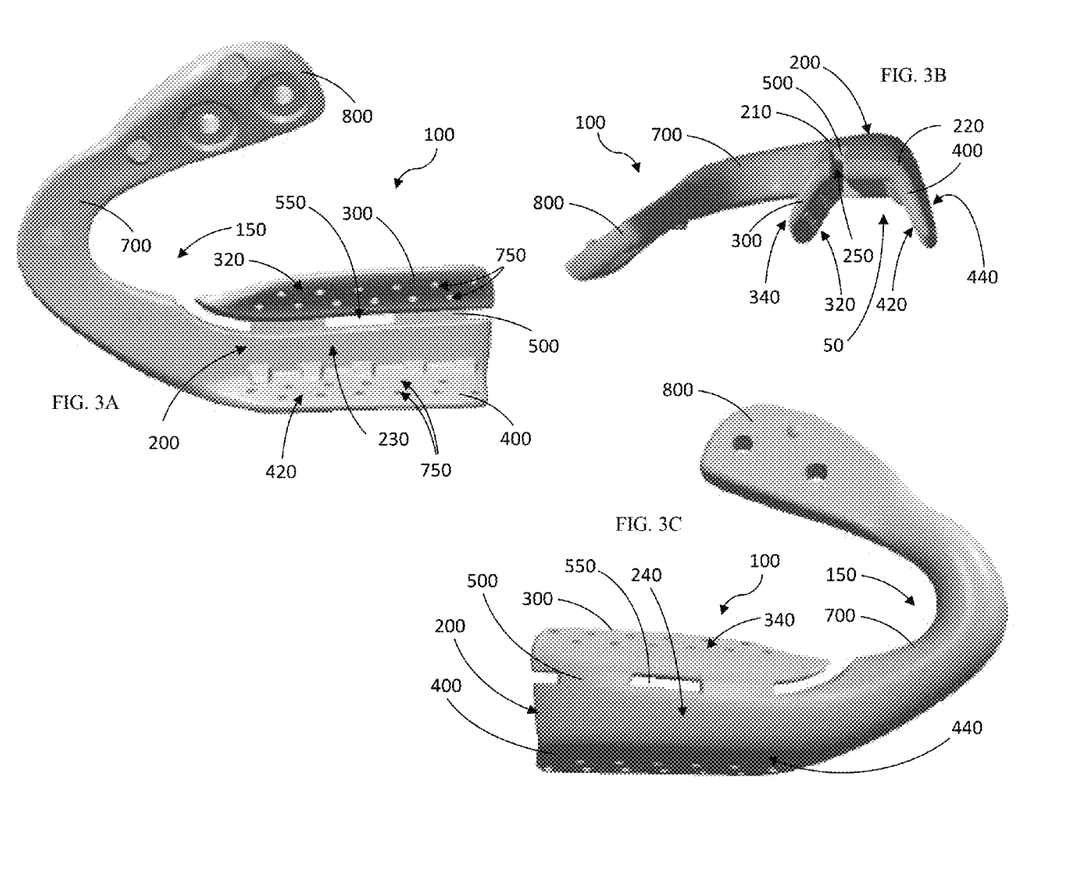
FIGS. 3A-3C schematically illustrate various views of a splint device configured to provide a fiducial marker and/or a tracking marker for a guidance system for a surgical robot, according to one aspect of the present disclosure.
Figures 4A, 4B, 4C:
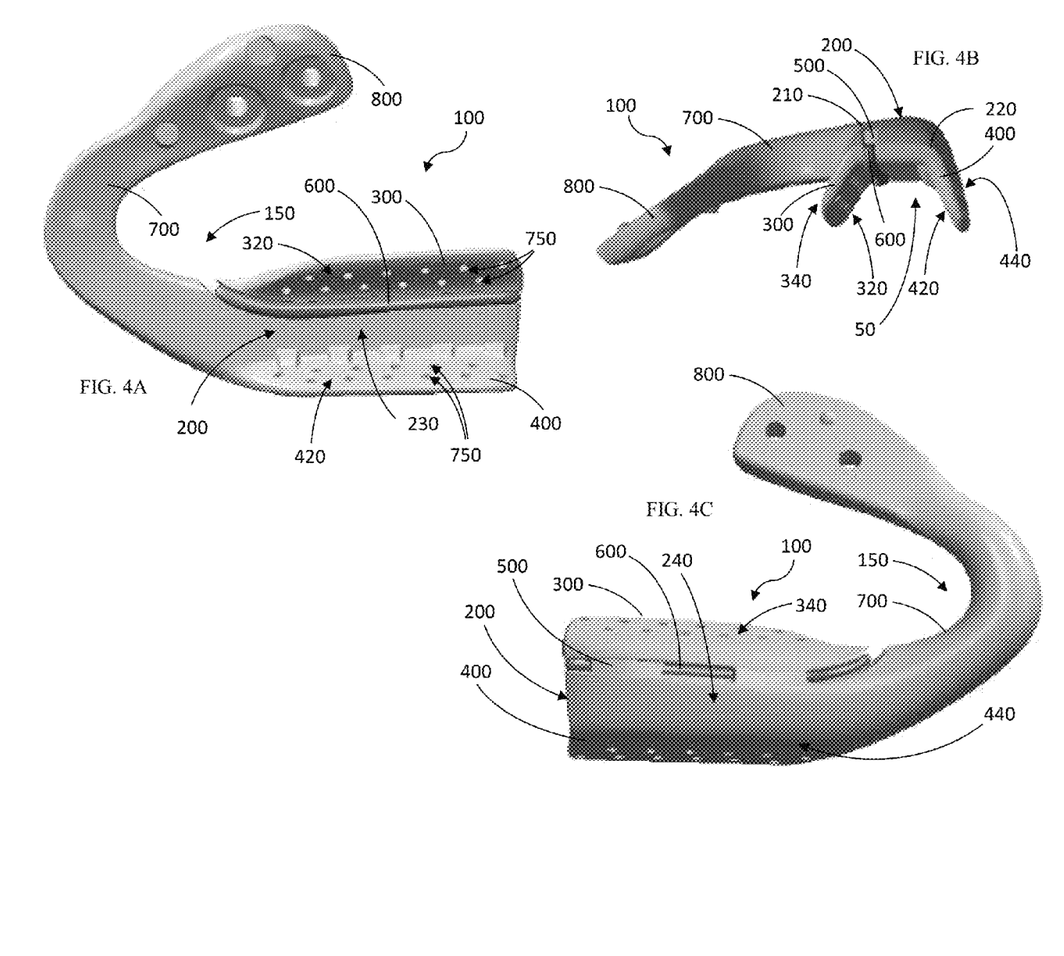
FIGS. 4A-4C schematically illustrate various views of a splint device, including a splint body and a partition member, configured to provide a fiducial marker and/or a tracking marker for a guidance system for a surgical robot, according to the aspect of the present disclosure shown in FIGS. 3A-3C.

Such prior art splint devices as shown, for example, in FIGS. 1, 2A, and 2B, also require a careful balance of the adhesive material (i.e., dental acrylic) to be applied in order to be effective in rigidly mounting the retainer portion to the teeth of the patient. For instance, if too little of the adhesive material is applied in the retainer portion, the splint device may be too easily separated from the teeth, since the amount of the adhesive material may not be sufficient to bond the retainer to the teeth to sufficiently resist the forces applied thereto during the surgical procedure. However, if too much of the adhesive material is applied to the retainer portion, the excess adhesive material may flows into the tooth undercuts (i.e., the portion of the tooth where the tooth narrows toward the gum-line and/or the spaces between teeth), the retainer portion will not be removable at the end of the surgical procedure, without, for instance, drilling into the solidified adhesive material to remove the retainer portion from the tooth/teeth. In such instances, the retainer portion will likely not be re-usable for the particular patient, and if further procedures are required, a new retainer portion, including a new mounting portion for the fiducial marker and/or tracking marker, may also be required.

As such, there exists a need for a splint device for forming a fiducial marker for the guidance system of a surgical robot used, for example, in dental surgery which addresses these and other limitations of prior art devices.

SUMMARY OF THE DISCLOSURE

The above and other needs are met by aspects of the present disclosure which, in one particular aspect, provides a splint device for use with a guidance system of a surgical robot, for example, for a surgical procedure associated with the head of a patient, such as dental surgery, neurosurgery, or ENT surgery. Such a device may comprise a laterally-extending medial portion having opposed lateral sides, and first and second stabilizing portions extending from the opposed lateral sides of the medial portion, with the medial portion and the first and second stabilizing portions cooperating to form a splint body defining a longitudinally-extending U channel. A bridge portion is defined by the medial portion, or by the medial portion and one of the first and second stabilizing portions, of the splint body, and the bridge portion extends longitudinally along the U channel. A partition member is configured to be received by the bridge portion, wherein the partition member extends from the bridge portion inwardly into and longitudinally along the U channel, between the first and second stabilizing portions.

Another aspect of the present disclosure provides a method of implementing a splint device for use with a guidance system of a surgical robot, for example, for a surgical procedure associated with the head of a patient, such as dental surgery, neurosurgery, or ENT surgery. The splint device includes a laterally-extending medial portion having opposed lateral sides, and first and second stabilizing portions extending from the opposed lateral sides of the medial portion. The medial portion and the first and second stabilizing portions cooperate to form a splint body defining a longitudinally-extending U channel. In addition, the medial portion, or the medial portion and one of the first and second stabilizing portions, of the splint body define a bridge portion extending longitudinally along the U channel. Such a method involving the splint device comprises engaging a partition member with the bridge portion, wherein the partition member extends from the bridge portion inwardly into and longitudinally along the U channel, between the first and second stabilizing portions. An adhesive material is engaged with the splint body, within the U channel defined thereby. The U channel of the splint body is engaged about a tooth or jaw of a patient, and the splint body urged toward the tooth or jaw, such that the partition member engages the tooth or jaw and separates the adhesive material into a first portion thereof engaged with the first stabilizing portion and a second portion thereof engaged with the second stabilizing portion.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE SEVERAL
VIEWS OF THE DRAWING(S)

Having thus described the disclosure in general terms, reference will now be made to the accompanying drawings, which are not necessarily drawn to scale, and wherein:

DETAILED DESCRIPTION OF THE
DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Particular aspects of the present disclosure, as shown, for example, in FIGS. 3A-3C and 4A-4C, provide a splint device 100 for use with a guidance system of a surgical robot, for instance, for dental surgery. One skilled in the art, however, will appreciate that the concept of the splint device disclosed herein as forming a fiducial marker and/or a tracking marker, or otherwise a frame of reference for a surgical robotic system may find applicability to other surgical processes not involving dental surgery, such as, for example, orthopedic surgery, ENT surgery, and neurosurgery. As such, the aspects of the disclosure presented herein are merely examples of the applicability of the disclosed concepts and are not intended to be limiting in any manner.

In one aspect, such a splint device 100 may comprise, for example, a laterally-extending medial portion 200 having opposed lateral sides 210, 220, and first and second stabilizing portions 300, 400 extending from the opposed lateral sides 210, 220 of the medial portion 200. The medial portion 200 and the first and second stabilizing portions 300, 400 thereby cooperate to form a splint body 150 defining a longitudinally-extending U channel 50 therein. A bridge portion 500 is defined by the medial portion 200, or by the medial portion 200 and one of the first and second stabilizing portions 300, 400, of the splint body 150, wherein the bridge portion 500 is configured to extending longitudinally along the U channel 50. A partition member 600 is configured to be received by the bridge portion 500. On being received by the bridge portion 500, the partition member 600 extends from the bridge portion 500 inwardly into (i.e., protrudes into) and longitudinally along the U channel 50, between the first and second stabilizing portions 300, 400.

In some aspects, a mounting portion 700 may be engaged with the splint body 150 and, in particular aspects, the mounting portion 700 may be further configured to extend outwardly from the splint body 150 and outwardly from the U channel 50. That is, the mounting portion 700 (i.e., mounting arm) extends from the splint body 150, to connect the splint body 150 to a kinematic mount 800. The kinematic mount 800, itself, may comprise an attachment point for a tracking portion (or tracking arm or other tracking provision) associated with the guidance system for the surgical robot (i.e., wherein, for instance, reflective markers may be mounted to the attachment point for optical tracking of the fiducial marker or the splint device itself, or the attachment point may include a securing site for forming a mechanical connection therewith for mechanical tracking of the fiducial marker, or the attachment point may otherwise be configured to receive an appropriate element associated with any other suitable tracking arrangement for the fiducial marker). In other aspects, the kinematic mount 800 may be configured or otherwise arranged to function as a fixed mounting site for particular tracking devices such as, for example, one or more markers that may be permanently affixed to the kinematic mount 800 and configured to be trackable by an optical-type tracking device (i.e., an optical tracking marker).

In some aspects, the medial portion 200 includes opposed inward and outward surfaces 230, 240 extending between the lateral sides 210, 220. The inward and outward surfaces 230, 240 cooperate to define a medial portion section thickness therebetween. In some instances, the bridge portion 500 has a decreased thickness relative to the section thickness of the medial portion 200. More particularly, in one aspect, the bridge portion 500 is decreased in section thickness from the inward surface 230 toward the outward surface 240 of the medial portion 200. Accordingly, in such instances, the medial portion 200 and the bridge portion 500 cooperate to define a bridge channel 250 configured to receive the partition member 600 therein, for example, in a friction fit. In another aspect, in addition to or instead of partition member 600 being received in a friction fit within the bridge channel 250, the bridge portion 500 defines one or more perforations 550 along a portion of a length thereof. In such instances, the partition member 600 is configured to engage the perforations 550 so as to be retained within the U channel 50. That is, the perforations 550 are configured to interact with corresponding provisions associated with the partition member 600 in order to secure the partition member 600 to the bridge portion 500 (i.e., such that the partition member 600 is retained by the bridge portion 500, for example, by a snap fit arrangement).

The first and second stabilizing portions 300, 400 each include opposed inward surfaces 320, 420 and outward surfaces 340, 440 extending from the respective lateral side 210, 220 of the medial portion 200. The inward and outward surfaces define therebetween a respective first and second stabilizing portion section thickness. In some aspects, the bridge portion 250 has a decreased thickness relative to the medial portion section thickness or the first or second stabilizing portion section thickness. In particular aspects, the bridge portion 500 is decreased in thickness from the inward surface 230 toward the outward surface 240 of the medial portion 200, or from the inward surface 320, 420 toward the outward surface 340, 440 of the first or second stabilizing portion 300, 400, respectively. That is, the bridge portion 500 may be defined by the medial portion 200, or by one of the stabilizing portions 300, 400, or by cooperation between the medial portion 200 and one of the first and second stabilizing portions 300, 400. As such, the medial portion 200, the first or second stabilizing portion 300, 400, and the bridge portion 500, either separately or in combination, define the bridge channel 250 configured to receive the partition member 600 therein.

In some aspects, as previously disclosed and shown, for example, in FIGS. 3A-3C and 4A-4C, the first and second stabilizing portions 300, 400 are engaged with the medial portion 200 so as to be generally opposed to and laterally spaced from each other. As such, the inner surfaces 320, 420 of the first and second stabilizing portions 300, 400 are generally opposed to and laterally spaced apart from each other, and cooperate with the medial portion to define the U channel 50. The U channel 50 may generally be in the form of, for example, a "U" channel or an inverted "U" channel, as appropriate or desirable for mounting, for example, to the mouth/teeth/jaw of a patient. For example, an inverted "U" channel may be applicable to the lower jaw or lower teeth of a patient, while a "U" channel may be applicable to the upper jaw or upper teeth of a patient. Upon being mounted to the mouth/teeth/jaw of the patient, the mounting portion 700 is disposed externally to the U channel 50 and extends outwardly of the U channel 50.

In some aspects, as shown, for example, in FIGS. 3A-3C and 4A-4C, the first and second stabilizing portion 300, 400 each extend at least 90 degrees with respect the medial portion 200. As such, the first and second stabilizer portions 300, 400 diverge from the respective first ends thereof engaged with the bridge portion 200, toward respective free or unattached second ends thereof. One skilled in the art will appreciate, however, that the engagement angle between the respective stabilizing portion and the bridge portion may vary as necessary or desired, according to the aspects of the present disclosure herein. For example, the engagement angle between one of the first and second stabilizing portions and the bridge portion may not necessarily be the same as the engagement angle between the other of the first and second stabilizing portions and the bridge portion. In other instances, the engagement angle between the stabilizing portion and the bridge portion may be about 90 degrees or less than 90 degrees.

Figure 5A:
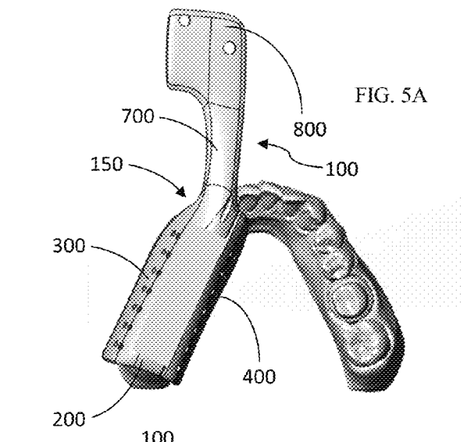
FIGS. 5A and 5B schematically illustrate a representative splint device engaged with a representative model of the mouth of the patient so as to provide a fiducial marker and/or a tracking marker for a guidance system for a surgical robot, according to one aspect of the present disclosure.
Figure 5B:
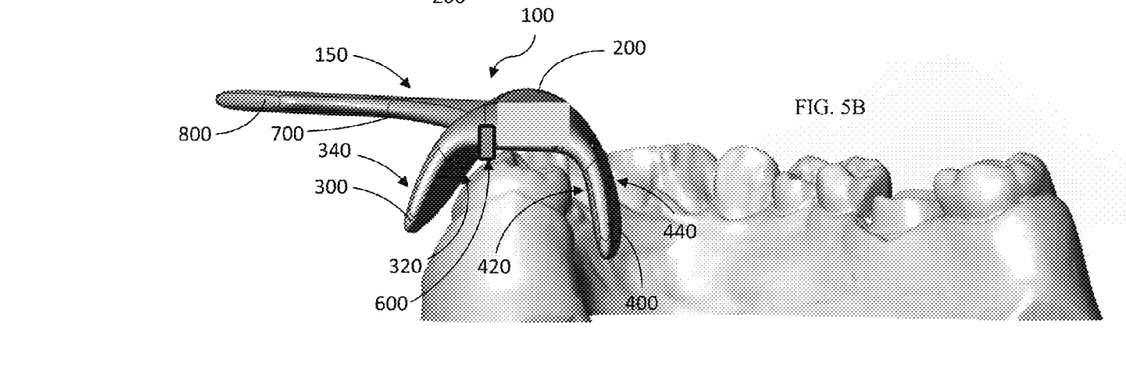

The U channel 50 may extend lengthwise, for example, over one tooth or over a plurality of teeth or along a portion of a jaw in the mouth of the patient. As shown in FIGS. 5A and 5B, in one instance, the U channel 50 may extend over a plurality of teeth in the mouth of the patient. In some aspects of the present disclosure, the splint device 100, including the splint body 150 and the partition member 600, may cooperate to perform a similar function as associated with prior art splint devices. More particularly, the U channel 50 having the partition member 600 installed therein, is further configured to receive an adhesive material therein so as to facilitate engagement with and adherence to a structure such as, for example, the tooth/teeth or jaw of a patient.

Once the adhesive material is received within the U channel 50, the splint device 100 is applied to the tooth/teeth or jaw of the patient, and the medial portion 200 is urged toward the tooth/teeth or jaw, until the partition member 600 abuts or is seated against the tooth/teeth or jaw. In doing so, the adhesive material disposed within the U channel 50, upon engagement of the splint body 150 about the tooth/teeth or jaw of the patient and urging of the splint body 150 toward the tooth/teeth or jaw, is separated into a first portion of the adhesive material engaged with the first stabilizing portion 300 (i.e., a portion of the adhesive material disposed between the first stabilizing portion 300 and the tooth/teeth or jaw) and a second portion of the adhesive material engaged with the second stabilizing portion 400 (i.e., a portion of the adhesive material disposed between the second stabilizing portion 400 and the tooth/teeth or jaw), by the partition member 600 engaging the tooth/teeth or jaw. In this regard, one skilled in the art will appreciate that the edge of the partition member 600 engaging the tooth/teeth or jaw of the patient may be pre-configured to match or correspond to the contour of the particular surface(s) of the tooth/teeth or jaw with which it is engaged through, for example, imaging or surface contouring techniques.

In some aspects of the splint device 100 due, for example, to the separation or portioning of the adhesive material by the partition member, may be configured such that one of the first and second stabilizing portions 300, 400 (i.e., either or both of the stabilizing portions) defines one or more relief ports 750. The one or more relief ports 750 are configured to cooperate with the partition member 600 such that, in the process of the partition member 600 engaging the tooth/teeth or jaw, any excess adhesive material within the U channel 50 is relieved from the U channel 50 through the one or more relief ports 750.

According to aspects of the present disclosure, when it is desirable to remove the splint device 100 from the mouth of the patient, the first and second stabilizing portions 300, 400 may be disengaged from each other, and individually removed, without the limitations of prior art splint devices. For example, even if more of the adhesive material (i.e., dental acrylic) than necessary is used to secure the splint device 100 to the teeth of the patient, excess adhesive material is relieved by flowing outwardly of the one or more relief ports 750. Accordingly, with the partition member 600 separating the adhesive material into the first and second portions, the first and second stabilizing portions 300, 400 may be disengaged from each other to allow removal of the splint device 100, without, for instance, drilling or cutting into the solidified adhesive material to remove the splint device from the tooth/teeth or jaw, as generally required with removal of prior art splint devices. That is, for example, even if more of the adhesive material (i.e., dental acrylic) than necessary is used to secure the splint device 100 to the tooth/teeth or jaw of the patient, and such excess adhesive material has flowed into the tooth undercuts (i.e., the portion of the tooth where the tooth narrows toward the gum-line and/or the spaces between teeth) more than generally necessary or desirable, the stabilizing portions 300, 400 of the splint device 100 may still be readily separated and removed at the end of the procedure. More particularly, in some aspects, the stabilizing portions 300, 400 may be readily separated from each other, for example, by cutting the medial portion 200 along the bridge portion 500. That is, by cutting longitudinally along and through the bridge portion 500 (i.e., to reach the partition member 600), the first and second stabilizing portions 300, 400 are separated by severing the medial portion 200 and its connection therebetween. The first and second stabilizing portions 300, 400, as well as the first and second portions of the adhesive material, respectively, securing the first and second stabilizing portions 300, 400 to the tooth/teeth or jaw, can then be individually removed from the tooth/teeth or jaw due to the discontinuity in the adhesive material.

Still another aspect of the present disclosure may comprise a method of implementing a splint device for use with a guidance system of a surgical robot, for example, for dental surgery (see, e.g., the process diagram shown in FIG. 6), wherein such a splint device may include a laterally-extending medial portion having opposed lateral sides, and first and second stabilizing portions extending from the opposed lateral sides of the medial portion, with the medial portion and the first and second stabilizing portions cooperating to form a splint body defining a longitudinally-extending U channel, and with the medial portion, or the medial portion and one of the first and second stabilizing portions, of the splint body defining a bridge portion extending longitudinally along the U channel.

Figure 6:
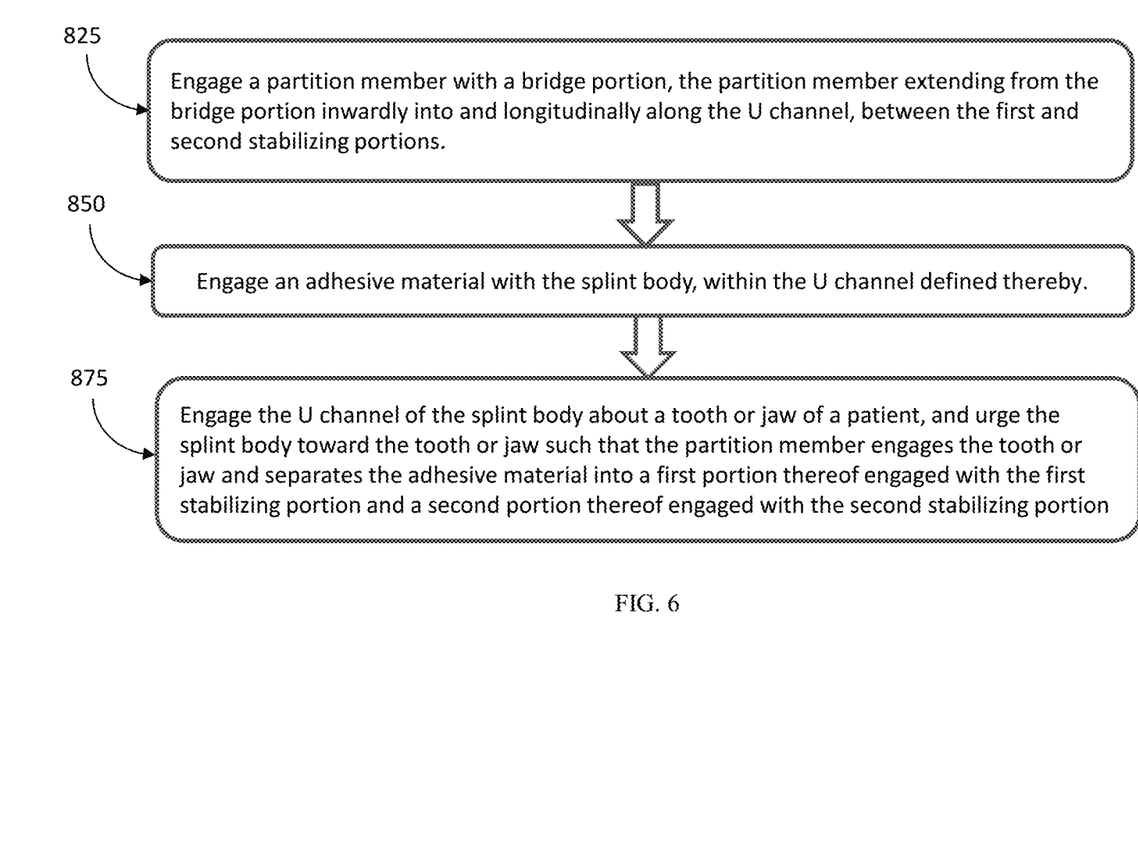
FIG. 6 schematically illustrates a method of implementing a splint device for use with a guidance system of a surgical robot, for example, for dental surgery, according to one aspect of the present disclosure.

Such a method may comprise engaging a partition member with the bridge portion of the splint body, with the partition member extending from the bridge portion inwardly into and longitudinally along the U channel, between the first and second stabilizing portions (block 825), and engaging an adhesive material with the splint body, within the U channel defined thereby (block 850). The U channel of the splint body is then engaged about a tooth or jaw of a patient, and the splint body urged toward the tooth or jaw such that the partition member engages the tooth or jaw and separates the adhesive material into a first portion thereof engaged with the first stabilizing portion and a second portion thereof engaged with the second stabilizing portion (block 875).

Further, in some instances, the medial portion 200 includes opposed inward and outward surfaces 230, 240 extending between the lateral sides 210, 220 thereof, wherein the inward and outward surfaces 230, 240 define a section thickness therebetween. The bridge portion 500 may thus be configured to have a decreased thickness relative to the section thickness of the medial portion 200, with the decrease extending from the inward surface 230 toward the outward surface 240 of the medial portion 200, wherein the medial portion 200 and the bridge portion 500 thereby define a bridge channel 250. As such, the step of engaging the partition member 600 with the bridge portion 500 comprises inserting the partition member 600 into the bridge channel 250. In other instances, the bridge portion 500 defines one or more perforations 750 along a portion of a length of the bridge portion 500. Accordingly, in such instances, the step of engaging the partition member 600 with the bridge portion 500 comprises engaging the partition member 600 with the one or more perforations 750 such that the partition member 600 is retained by the bridge portion 500.

In some aspects, the first and second stabilizing portions 300, 400 each include opposed inward surfaces 320, 420 and outward surfaces 340, 440 extending from the respective lateral sides 210, 220 of the medial portion 200, with the inward and outward surfaces defining a respective first and second stabilizing portion section thickness therebetween, wherein the bridge portion 500 is decreased in thickness from the inward surface 230 toward the outward surface 240 of the medial portion 200, or from the inward surface 320, 420 toward the outward surface 340, 440 of the first or second stabilizing portion 300, 400. As such, the medial portion 200, the first or second stabilizing portion 300, 400, and the bridge portion 500 thereby cooperate to define a bridge channel 250. Accordingly, the step of engaging the partition member 600 with the bridge portion 500 comprises inserting the partition member 600 into the bridge channel 250.

Further, in some aspects, the method may further comprise engaging a mounting portion 700 with the splint body 150, such that the mounting portion 700 extends outwardly of the U channel 50.

In still other aspects, one of the first and second stabilizing portions 300, 400 defines one or more relief ports 750. Accordingly, the step of engaging the U channel 50 of the splint body 150 about the tooth/teeth or jaw of the patient comprises engaging the U channel 50 of the splint body 150 about the tooth/teeth or jaw of the patient, and urging the splint body 150 toward the tooth/teeth or jaw such that the partition member 600 engages the tooth/teeth or jaw, and separates the adhesive material into the first portion of the adhesive material engaged between the first stabilizing portion 300 and the tooth/teeth or jaw, and the second portion of the adhesive material engaged between the second stabilizing portion 400 and the tooth/teeth or jaw, and wherein any excess adhesive material is relieved from the U channel 50 through the one or more relief ports 750.

Figure 7:
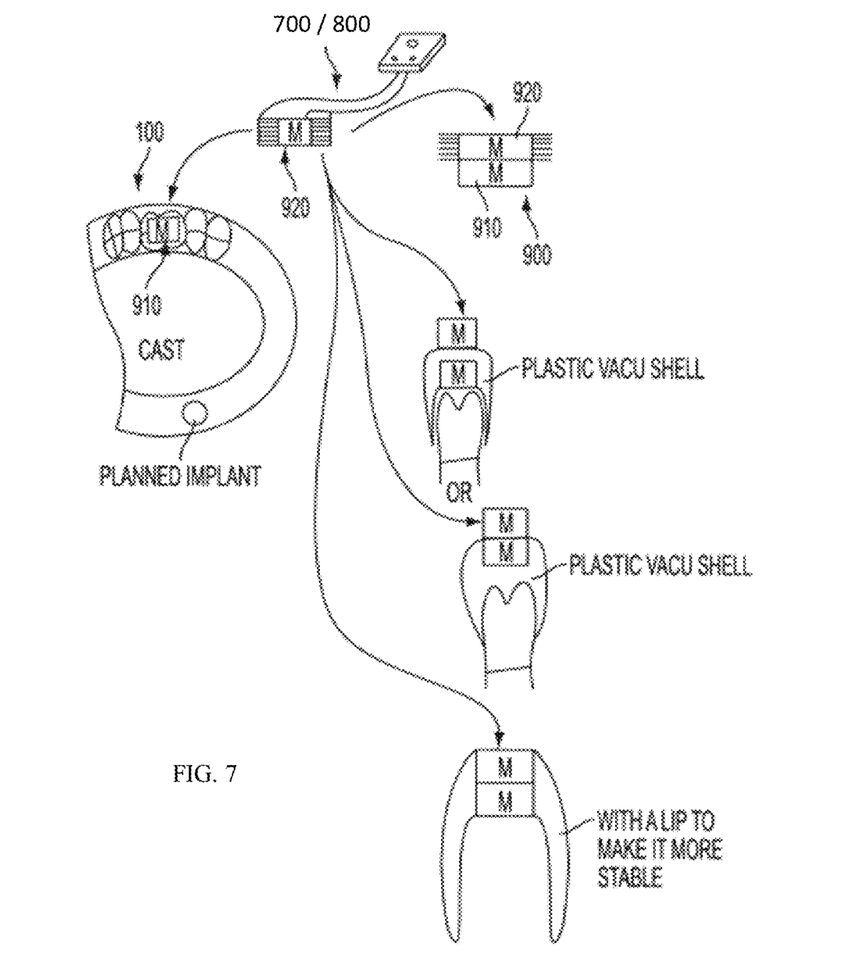
FIG. 7 schematically illustrates a molded polymeric splint device incorporating one portion of an engagement arrangement and a mounting portion/kinematic mount incorporating a complementary portion of the engagement arrangement, so as to provide a re-usable mounting portion/kinematic mount associated with a splint device, according to another aspect of the present disclosure.

In still further aspects of the present disclosure as shown, for example, in FIG. 7, the splint device 100 (or "retainer portion" of the disclosed device having the mounting portion 700 (or mounting arm) and/or the kinematic mount 800 engaged therewith) may comprise custom-molded arrangement comprised of a polymeric material (i.e., an acrylic or other suitable polymer). In some aspects, the splint body 150 and the partition member 600 may be molded to form the respective components of the splint device 100 otherwise disclosed herein. In other aspects, as necessary or desired, at least the splint body 150 (retainer portion) and the mounting portion 700 may be molded as a single integral element. In either instance, the splint device 100 may be molded from the selected polymer using, for example, a vacuum sealing or vacuum molding process implementing a rigid (i.e., stone or plaster) model (or basis of the mold) of the structure of the patient to which the splint device 100 is to be affixed.

Further, as shown, for example, in FIG. 7, the molded polymeric splint device 100 may incorporate one portion 910 of an engagement arrangement 900 and a mounting portion 700/kinematic mount 800 incorporating a complementary portion 920 of the engagement arrangement 900, so as to provide a re-usable mounting portion 700/kinematic mount 800 associated with the molded splint device 100. For example, the engagement arrangement may comprise a screw/nut or other complementary fastener configuration, wherein either of the screw/nut may be molded into the polymeric splint device 100, while the other of the screw/nut may be associated with the mounting portion 700/kinematic mount 800. One skilled in the art will otherwise appreciate that the one portion 910 of the engagement arrangement 900 may be incorporated into the splint device 100 in many different manners, and in many different locations associated with the molded polymeric splint device 100, and may be configure in many different manners. For example, in some aspects, a "nut" portion may not be necessary, but a threaded orifice may instead be provided in the polymeric splint device 100 or the mounting portion 700/kinematic mount 800. In still other instances, the "screw" portion may not be, for example, molded into the polymeric splint device 100, but instead, the splint device 100 may define an orifice configured to receive the "screw" portion therethrough for engagement with the "nut" portion or threaded orifice associated with the mounting portion 700/kinematic mount 800. In yet further instances, the engagement between the splint device 100 and the mounting portion 700/kinematic mount 800 may include alignment provisions to ensure proper alignment between the splint device 100 and the mounting portion 700/kinematic mount 800, upon engagement therebetween.

Also, in other aspects, the one portion 910 of the engagement arrangement 900 may comprise a first magnetic element, while the complementary portion 920 of the engagement arrangement 900 may comprise a second magnetic element associated with the mounting portion 700/kinematic mount 800. Either magnetic element may comprise, for example, a magnet or a magnetically-attractive material such as a metal. Such a configuration may allow, for instance, for the mounting portion 700/kinematic mount 800 to be re-usable and the splint device 100/retainer portion to be disposable. The one portion 910 of the engagement arrangement 900 may be incorporated into the molded polymeric splint device 100, for instance, in an "overmolding" process, as will be appreciated by one skilled in the art.

Many modifications and other embodiments of the inventions set forth herein will come to mind to one skilled in the art to which these disclosed embodiments pertain having the benefit of the teachings presented in the foregoing descriptions and the associated drawings. For example, the splint device 100, whether molded as a single piece or as two or more complementary pieces, may further be configured to roughly or approximately follow or conform to the tooth/teeth of the patient, including undercuts (i.e., the portion of the tooth where the tooth narrows toward the gum-line and/or the spaces between teeth) if necessary, wherein the lip, flange, or contour formed thereby in the splint device to conform to the tooth/teeth may facilitate stability of the splint device with respect to the corresponding structure of the patient (see, e.g., FIG. 7). In addition, even though an exemplary splint device is disclosed herein as being configured to engage the tooth/teeth/jaw on one side of the jaw of a patient, one skilled in the art will appreciate that a mirror image version of the splint device may be configured to engage the tooth/teeth/jaw on the contralateral side of the patient's jaw. Moreover, one skilled in the art will appreciate that an anterior version of the splint device may be configured to engage the tooth/teeth/jaw on the front teeth of the patient's jaw so as to allow bilateral surgery to be achieved.

Therefore, it is to be understood that embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A splint device for use with a guidance system of a surgical robot, said device comprising:

a laterally-extending medial portion having opposed lateral sides, and opposed inward and outward surfaces extending between the lateral sides, the inward and outward surfaces defining a section thickness therebetween;

first and second stabilizing portions extending from the opposed lateral sides of the medial portion, the medial portion and the first and second stabilizing portions cooperating to form a splint body defining a longitudinally-extending U channel;

a bridge portion defined by the medial portion, or by the medial portion and one of the first and second stabilizing portions, of the splint body and extending longitudinally along the U channel, the bridge portion being decreased in section thickness, relative to the section thickness of the medial portion, from the inward surface toward the outward surface of the medial portion, and the medial portion and the bridge portion thereby defining a bridge channel; and a partition member configured to be received by and within the bridge channel, the partition member extending from the bridge channel inwardly past the inward surface of the medial portion into and longitudinally along the U channel, between the first and second stabilizing portions, wherein one of the first and second stabilizing portions defines one or more relief ports, the one or more relief ports cooperating with the partition member such that an adhesive material disposed within the U channel, upon engagement of the splint body about a tooth or a jaw of a patient and urging the splint body toward the tooth or jaw, is separated into a first portion thereof engaged with the first stabilizing portion and a second portion thereof engaged with the second stabilizing portion, by the partition member engaging the tooth or jaw, and wherein any excess adhesive material is relieved from the U channel through the one or more relief ports.

2. The device of claim 1, wherein the bridge portion defines perforations along a portion of a length thereof, and the partition member is configured to engage the perforations from within the bridge channel so as to be retained by the bridge portion.

3. The device of claim 1, wherein the medial portion includes the opposed inward and outward surfaces extending between the lateral sides, with the inward and outward surfaces defining a medial portion section thickness therebetween, wherein the first and second stabilizing portions each include opposed inward and outward surfaces extending from the respective lateral side of the medial portion, with the inward and outward surfaces defining a respective first and second stabilizing portion section thickness therebetween, and wherein the bridge portion has a decreased thickness relative to the medial portion section thickness or the first or second stabilizing portion section thickness.

4. The device of claim 3, wherein the bridge portion is decreased in thickness from the inward surface toward the outward surface of the medial portion or the first or second stabilizing portion, and wherein the medial portion, the first or second stabilizing portion, and the bridge portion thereby defines the bridge channel configured to receive the partition member therein.

5. The device of claim 1, comprising a mounting portion engaged with the splint body and extending outwardly of the U channel.

6. A method of implementing a splint device for use with a guidance system of a surgical robot, the splint device including a laterally-extending medial portion having opposed lateral sides and opposed inward and outward surfaces extending between the lateral sides, the inward and outward surfaces defining a section thickness therebetween, and first and second stabilizing portions extending from the opposed lateral sides of the medial portion, with the medial portion and the first and second stabilizing portions cooperating to form a splint body defining a longitudinally-extending U channel, and with the medial portion, or the medial portion and one of the first and second stabilizing portions, of the splint body defining a bridge portion extending longitudinally along the U channel, the bridge portion being decreased in section thickness, relative to the section thickness of the medial portion, from the inward surface toward the outward surface of the medial portion, and the medial portion and the bridge portion thereby defining a bridge channel, said method comprising:

inserting a partition member into the bridge channel, the partition member extending from the bridge channel inwardly past the inward surface of the medial portion into and longitudinally along the U channel, between the first and second stabilizing portions;

engaging an adhesive material with the splint body, within the U channel defined thereby; and engaging the U channel of the splint body about a tooth or jaw of a patient, and urging the splint body toward the tooth or jaw such that the partition member engages the tooth or jaw and separates the adhesive material into a first portion thereof engaged with the first stabilizing portion and a second portion thereof engaged with the second stabilizing portion.

7. The method of claim 6, wherein the bridge portion defines perforations along a portion of a length thereof, and wherein inserting the partition member into the bridge channel comprises engaging the partition member with the perforations from within the bridge channel such that the partition member is retained by the bridge portion.

8. The method of claim 6, wherein the medial portion includes the opposed inward and outward surfaces extending between the lateral sides, with the inward and outward surfaces defining a medial portion section thickness therebetween, wherein the first and second stabilizing portions each include opposed inward and outward surfaces extending from the respective lateral side of the medial portion, with the inward and outward surfaces defining a respective first and second stabilizing portion section thickness therebetween, wherein the bridge portion is decreased in thickness from the inward surface toward the outward surface of the medial portion or the first or second stabilizing portion, wherein inserting the partition member into the bridge channel comprises inserting the partition member into the bridge channel defined by the medial portion, the first or second stabilizing portion, and the bridge portion.

9. The method of claim 6, comprising engaging a mounting portion with the splint body, such that the mounting portion extends outwardly of the U channel.

10. The method of claim 6, wherein one of the first and second stabilizing portions defines one or more relief ports, and wherein engaging the U channel of the splint body about the tooth or jaw of the patient comprises urging the splint body toward the tooth or jaw such that the partition member separates the adhesive material into the first portion thereof engaged with the first stabilizing portion and the second portion thereof engaged with the second stabilizing portion, and such that any excess adhesive material is relieved from the U channel through the one or more relief ports.

* * * * *